(12) United States Patent
Trovato et al.

(10) Patent No.: US 8,597,278 B2
(45) Date of Patent: Dec. 3, 2013

(54) MEDICAMENT DELIVERY SYSTEM AND PROCESS

(75) Inventors: Karen I. Trovato, Putnam Valley, NY (US); Jeff Shimizu, Cortlandt Manor, NY (US)

(73) Assignee: Medimetrics Personalized Drug Delivery B.V., Eindhoven (NL)

( * ) Notice: Subject to any disclaimer, the term of this patent is extended or adjusted under 35 U.S.C. 154(b) by 822 days.

(21) Appl. No.: 12/306,017

(22) PCT Filed: Apr. 12, 2007

(86) PCT No.: PCT/IB2007/051321
§ 371 (c)(1),
(2), (4) Date: Dec. 22, 2008

(87) PCT Pub. No.: WO2008/012700
PCT Pub. Date: Jan. 31, 2008

(65) Prior Publication Data
US 2009/0306632 A1 Dec. 10, 2009

Related U.S. Application Data

(60) Provisional application No. 60/805,645, filed on Jun. 23, 2006.

(51) Int. Cl.
*A61K 9/22* (2006.01)

(52) U.S. Cl.
USPC ........................................ 604/890.1

(58) Field of Classification Search
USPC ............... 604/19, 890.1, 892.1, 93.01, 891.1
See application file for complete search history.

(56) References Cited

U.S. PATENT DOCUMENTS

| | | | |
|---|---|---|---|
| 5,170,801 A * | 12/1992 | Casper et al. | 600/582 |
| 5,604,531 A | 2/1997 | Iddan | |
| 5,846,188 A * | 12/1998 | Palti | 600/300 |
| 6,632,216 B2 | 10/2003 | Houzego | |
| 6,929,636 B1 * | 8/2005 | von Alten | 604/890.1 |
| 7,061,523 B2 * | 6/2006 | Fujita et al. | 348/77 |
| 2003/0073935 A1 | 4/2003 | Segawa | |
| 2003/0085994 A1 * | 5/2003 | Fujita et al. | 348/77 |
| 2003/0167000 A1 | 9/2003 | Mullick | |
| 2004/0122315 A1 * | 6/2004 | Krill | 600/437 |
| 2005/0148847 A1 * | 7/2005 | Uchiyama et al. | 600/407 |
| 2005/0195118 A1 | 9/2005 | Ito | |
| 2006/0155174 A1 * | 7/2006 | Glukhovsky et al. | 600/301 |

FOREIGN PATENT DOCUMENTS

| | | |
|---|---|---|
| WO | 02082979 A2 | 10/2002 |
| WO | 2004091361 A2 | 10/2004 |
| WO | 2005092189 A1 | 10/2005 |
| WO | 2006021932 A1 | 3/2006 |
| WO | 2006025013 A1 | 3/2006 |
| WO | 2006077527 A2 | 7/2006 |
| WO | 2006077528 A2 | 7/2006 |
| WO | 2006077529 A2 | 7/2006 |
| WO | 2006077530 A2 | 7/2006 |
| WO | 2007057838 A1 | 5/2007 |

* cited by examiner

*Primary Examiner* — Kevin C Sirmons
*Assistant Examiner* — Shefali Patel
(74) *Attorney, Agent, or Firm* — Lee & Hayes, PLLC (57) ABSTRACT

A system and method for delivering a substance to a selected site in an alimentary canal of a human or animal includes an ingestible capsule. The capsule has a compartment for storing the substance; a receiver suitable for receiving a signal through animal tissue; a processor for storing a programmed set of instructions; and an electronic power source. The system and method further has at least one transmitter, disposed on a medically relevant site on a body of the human or animal, for sending the signal to the receiver. The receiver includes a proximity based detector for measuring proximity of the receiver to the at least one transmitter, and the processor instructs a releasing device of the capsule to release the substance upon recognition of a pre-programmed pattern of signals.

15 Claims, 5 Drawing Sheets

MEDICAMENT DELIVERY SYSTEM AND PROCESS

RELATED REFERENCES

This application is a National Stage Application under 35 USC §371 of PCT Application No. PCT/IB2007/051321, filed Apr. 12, 2007, which claims priority to U.S. Provisional Patent Application No. 60/805,645, filed Jun. 23, 2006. The present disclosure is related to U.S. Provisional Patent Application No. 60/644,540, entitled "Electronically Controlled Capsule For Releasing Radiation", and filed Jan. 18, 2005, U.S. Provisional Patent Application No. 60/644,539, entitled "Electronically Controlled Capsule", and filed Jan. 18, 2005, U.S. Provisional Patent Application No. 60/644,538, entitled "Electronically Controlled Ingestible Capsule", and filed Jan. 18, 2005, U.S. Provisional Patent Application No. 60/644,518, entitled "System And Method For Controlling Traversal Of An Ingested Capsule", and filed Jan. 18, 2005, U.S. Provisional Patent Application No. 60/606,276, entitled "Electronically Controlled Pill And System For Delivering At Least One Medicament", and filed Sep. 1, 2004, U.S. Provisional Patent Application No. 60/605,364, entitled "Electronically And Remotely Controlled Pill And System For Delivering At Least One Medicament", and filed Aug. 27, 2004, and U.S. Provisional Patent Application No. 60/738,238, entitled "System and Method for Interacting With a Cell or Tissue", and filed Nov. 18, 2005, with each of the foregoing references being assigned to the Assignee of the present disclosure and hereby being expressly incorporated by reference as part hereof.

The present invention relates to a system and process for accurate and reliable delivery of a controlled quantity of a substance. More particularly, the present invention relates to a system and process for accurate targeting of medication delivery to selected sites in the alimentary canal of a human or animal.

Treatment of a disease, ailment or condition typically requires targeting a specific area of the body requiring treatment. This is particularly true of diseases or conditions of the gastrointestinal tract. A medicament generally traverses the gastrointestinal tract where it is absorbed for treating the condition. Many conditions of the gastrointestinal tract, which require precisely targeted treatment exist.

Inflammatory Bowel Diseases (IBDs) are one such group of gastrointestinal illnesses which require targeted treatment. IBDs are chronic autoimmune diseases of unknown etiology. Approximately one million Americans and one million Europeans suffer from these types of diseases. Crohn's disease is a common IBD that is characterized by chronic inflammation of the intestinal tract. Crohn's disease can occur anywhere in the digestive tract, often spreading deep into the layers of affected tissues. Another common IBD is ulcerative colitis. Ulcerative colitis, primarily affects the innermost lining of the large intestine and rectum. IBD diseases can be both painful and debilitating, may lead to life-threatening complications, and have no known medical cure. Severe cases of IBD may require surgery, such as bowel resection, strictureplasty or temporary or permanent colostomy or ileostomy. For these reasons, treatment for these diseases is costly.

All forms of IBD may require immunosuppression to control the symptoms. Many successful treatments require delivery of a medicament directly to the location of the distress. Accordingly, current treatments of IBDs require precise delivery of medicaments to selected sites in the alimentary canal. Among the common drug treatments are delayed release capsules containing mesalazine, steroids, and immunomodulators (such as azathioprine, methotrexate or 6-mercaptopurine) or biologicals. Such delayed release capsules rely on chemical breakdown to determine the time of release. These capsules are typically manufactured from a material that dissolves in a particular specific environment and/or within a particular time period within the alimentary canal. Capsules for targeting treatment areas have achieved varying forms of success. Conventional targeting strategies are described in the *Encyclopedia of Controlled Drug Delivery* by Edith Mathiowtz, published by John Wiley & Sons, incorporated by reference herein.

However, for dissolving type timed delivery capsules, the delivery of the medicament is highly dependent upon the predictability of the particular environment to which the capsule containing the medicament is subjected, as well as to nuances such as folds in the intestine or the position of the stomach, which may create disruptions in passage of the capsule. Due to the unpredictability of the alimentary canal environment and the disruption of passage caused by the geography of the canal, dissolving type capsules, while useful for non-precise release of medicaments in general areas of the alimentary canal, do not provide viable means for site-specific medicament delivery, as is required for successful treatment of IBDs.

Alternative approaches to targeting specific areas of the alimentary canal include means for targeting the rectum and lower descending colon through the use of suppositories, enemas and foams. However, these methods are burdensome to the patient. One such treatment for Ulcerative Colitis illustrates this problem by requiring twice daily enemas of amniosalicylates or corticosteriods. The procedure further requires that the patient lie on his side for an hour in the morning and an hour in the evening to retain the medication in the distal colon.

Eectronic pills have also been employed for drug delivery. A recent example is described in U.S. Pat. No. 6,632,216 to Houzego et al. Houzego is directed to an ingestible capsule for delivering a substance to the gastrointestinal tract of a mammal having a receiver of electromagnetic radiation for powering an openable part of the capsule to an opened position for dispensing of the substance. The capsule disclosed by Houzego et al. is a complex mechanism requiring a series of antennae. The capsule, therefore, suffers several disadvantages. Principal amongst these is the complexity of the wearable apparatus which makes the capsule expensive to manufacture. The complexity of the capsule further renders it prone to malfunction.

Another electronic pill is described in U.S. Patent Application Publication 2004/0122315 to Krill. Krill discloses a medical capsule having at least one ultrasonic transducer electrically connected to a transceiver(s) and a means for wireless communication between a capsule ingested or implanted in a living body and an external network. The wireless communication of Krill is achieved by means of ultrasound, generally in the range of 5-20 MHz, using miniature acoustic transducers. However, ultrasonic means for communication between an ingested capsule and an external network suffers from several drawbacks. Ultrasound does not propagate through the hollow spaces in the stomach. Additionally, the pill disclosed by Krill is impractical in that piezoelectric transducers are expensive to manufacture, require a large area and a high voltage.

A need therefore exists for a simple, convenient and reliable oral means for drug delivery to selected sites in the alimentary canal. A need also exists for reliable oral means for drug delivery to the lower part of the gastrointestinal tract, specifically the colon.

A need further exists for reliable means for simple, convenient and reliable delivery of medicaments to specific alimentary canal sites, particularly means that might be accurately and repeatedly accomplished without confining the patient to a medical facility and without requiring the intensity of medical professional attention now required by typically available means.

It is an object of the present invention to provide a simple and convenient means for accurate and reliable delivery of a controlled quantity of a substance, such as a pharmaceutically active compound, foodstuff, dye, radio labeled marker, vaccine, physiological marker or diagnostic agent to a selected site in the alimentary canal of human or animal.

It is also an object of the invention to provide a simple means for accurate and reliable delivery of a controlled quantity of a substance to the lower gastrointestinal tract, especially the colon, of a human or animal.

It is additionally an object of the invention to provide a simple means for determining the location of an electronic pill that has been ingested by a subject.

It is a further object of the invention to provide a simple means for dispensing a controlled quantity of a substance when the electronic pill has reached a predetermined location in the alimentary canal of the subject.

These and other objects and advantages of the present invention are achieved by a system for delivering a substance to a selected site in the alimentary canal of a human or animal comprising: an ingestible capsule comprising: a compartment for storing the substance; a releasing means for releasing the substance from the compartment; a receiver suitable for receiving a signal through animal tissue; a processor for storing a programmed set of instructions; and an electronic power source; and at least one transmitter, disposed on a medically relevant site on the body of the human or animal, for sending a signal to the receiver, wherein the receiver further comprises a proximity based detection means for measuring proximity of the receiver to the at least one transmitter, and wherein the processor instructs the releasing means to release the substance upon recognition of a pre-programmed pattern of transmitters.

There is also provided a process for delivery of a substance to a selected site in the alimentary canal of a human or animal, comprising: a step of determining the selected site of the alimentary canal to be targeted by clinical means; a step of providing an ingestible capsule comprising: a compartment for storing the substance; a releasing means for releasing the substance from the storage compartment; a receiver suitable for receiving a signal through animal tissue, the receiver further comprising a proximity based detection means for measuring the proximity of the receiver to a signaling transmitter; a processor for storing a programmed set of instructions; and an electronic power source; a step of programming the capsule with instructions for release of the substance, the instructions comprising at least the recognition of a pattern of signaling transmitters, the pattern being designed to identify the selected site; and a step of providing a wearable apparatus that is attachable to the body of the human or animal, the wearable apparatus having at least one transmitter for sending a signal to the receiver; wherein the receiver proximity based detection means identifies the location of the ingested capsule within the alimentary canal of the human or animal by measuring the signal strength of the at least one transmitter, and wherein the processor instructs the releasing means to release the substance upon recognition of a pre-programmed pattern of transmitters.

The foregoing and still other objects and advantages of the present invention will be more apparent from the following detailed explanation of the preferred embodiments of the invention in connection with the accompanying drawings.

A system and method for delivering a substance to a selected site in the alimentary canal of a subject human or animal is provided. Specifically, a simple system and method for determining the location of an ingested capsule within the alimentary canal and for instructing the ingested capsule to deliver a payload when a predetermined site is reached is provided. As used herein and in the claims the words "substance" and "payload" refer to medicines, non-medicinal substances, contrast agents, gases, fluids, liquids, chemicals, radiological agents, imaging markers, sensors for monitoring vitals, etc.

Figure 1:
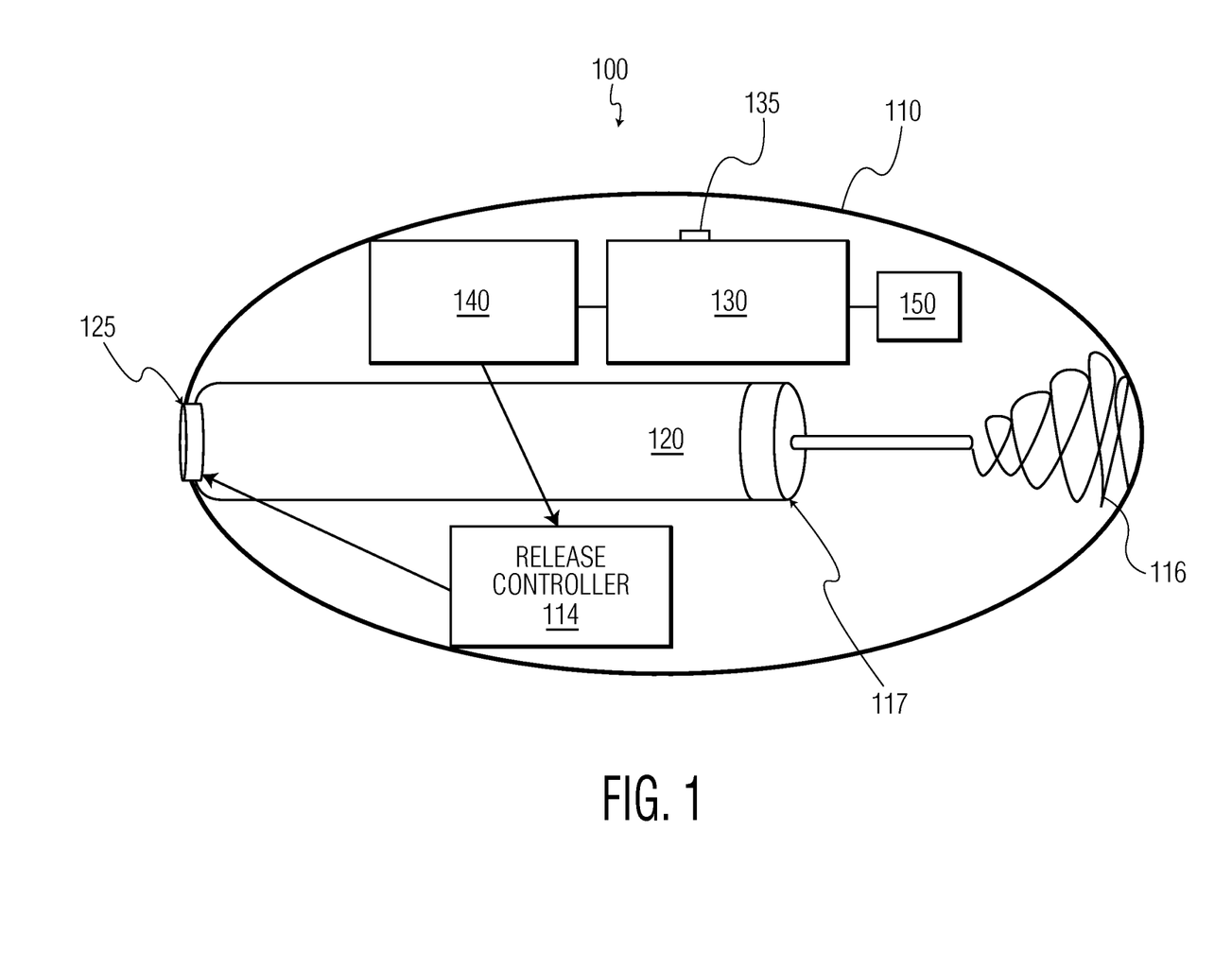
FIG. 1 is a schematic diagram of an electronic pill in accordance with the present invention.

Referring to the drawings and, in particular, FIG. 1, there is illustrated an ingestible capsule according to the present invention generally represented by reference numeral 100. Capsule 100 is a self-contained, electronically controlled medicament delivery system for ingestion by a subject human or animal 300. As described in detail below, capsule 100 includes programmed electronics that control a release mechanism for dispensing a substance upon recognition of a programmed dispensing pattern.

Figure 2:
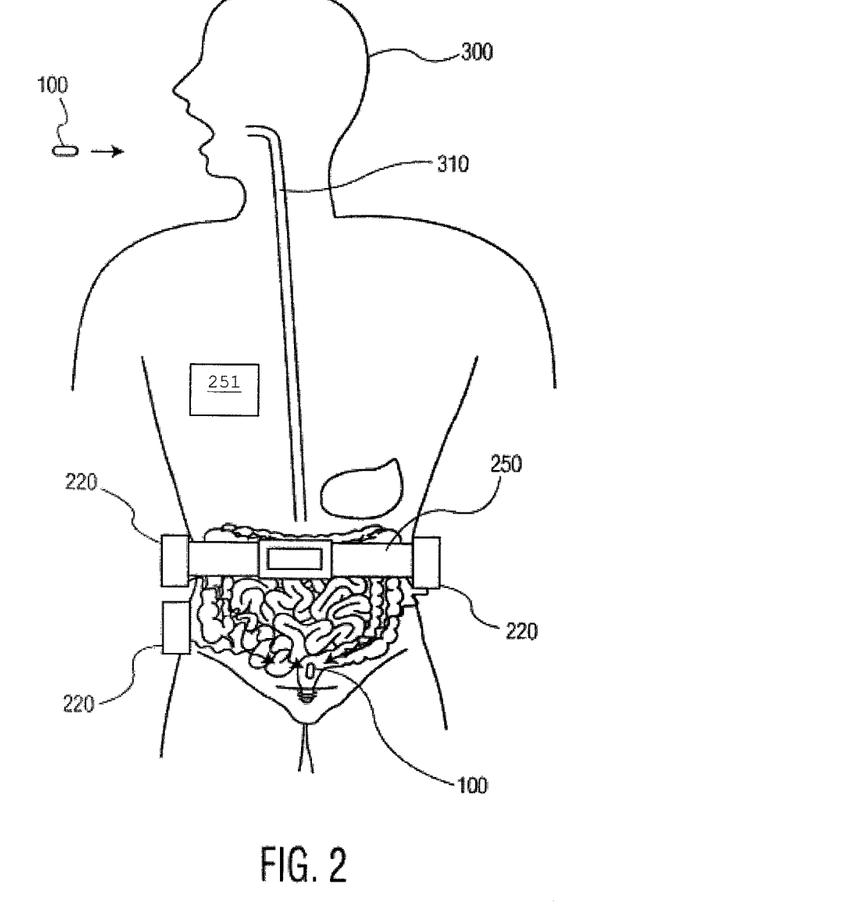
FIG. 2 is a diagrammatic view illustrating an exemplary pattern of transmitters for monitoring the positioning of the capsule in the body of a human subject.
Figure 3:
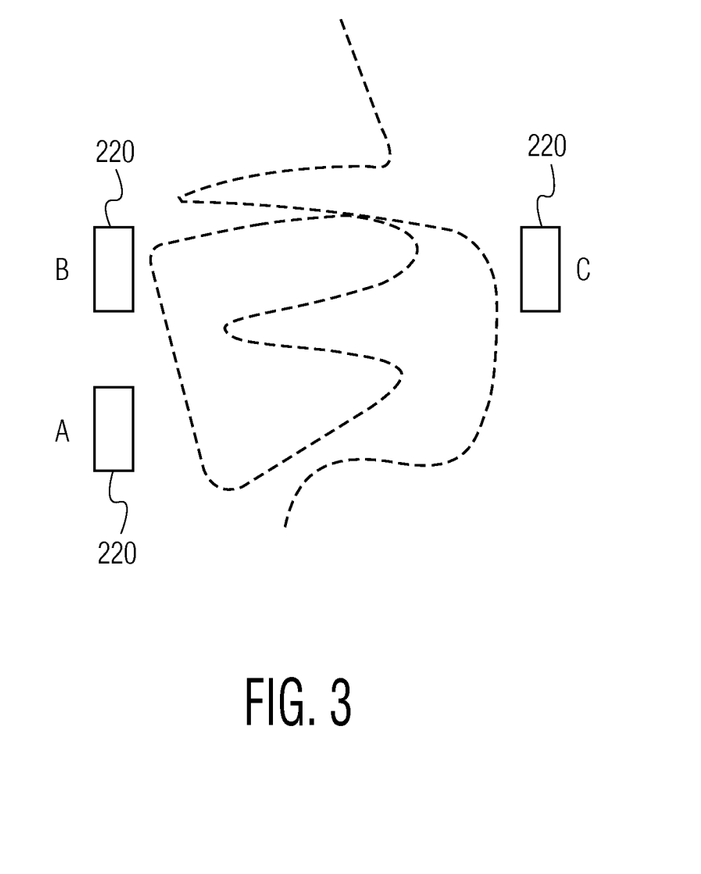
FIG. 3 is an internal diagrammatic view illustrating a simple pattern of transmitters for identifying selected sites in the gastrointestinal tract of a human subject.

As shown in FIGS. 2 and 3, at least one transmitter(s) 220 is attachable to predetermined medically relevant locations on the body of subject 300. Any number of transmitter(s) 220 may be employed. A receiver 130 determines the location of capsule 100 in relation to transmitter(s) 220 by proximity based detection means.

Referring again to FIG. 1, capsule 100 includes an outer shell or housing 110; a receiver 130 for receiving a signal from transmitter(s) 220; a signal strength indicator or meter 135 for determining the proximity of receiver 130 to transmitter(s) 220; control circuitry 140 for storing a programmed set of instructions and for processing information received by receiver 130; a power source 150; and a storage compartment or reservoir 120, for storing a substance Capsule 100 is preferably sized to be suitable to be swallowed by a human or animal. Housing 110 is preferably made from bio-compatibles materials such that capsule 100 is biocompatible for at least the amount of time it requires to traverse the gastrointestinal tract of a human or animal. The bio-compatible materials are preferably stable in room temperature, such that capsule 100 has a long shelf life. Housing 110 may be fabricated from a biologically safe polymeric material such as, for example, polytetrafluoroethylene, polyethylene, acrylics and the like. Housing 110 is more preferably manufactured from materials used to fabricate implantable devices, including pacemaker leads and cardiac prosthesis devices, such as artificial hearts, heart valves, intraaortic balloons, and ventricular assist devices. These materials include Pellethane® 2363 polyetherurethane series of materials available from Dow Chemical Company and Elasthane polyetherurethane available from the Polymer Technology Group, Inc. Other materials include PurSil® and CarboSil® also available from the Polymer Technology Group, Inc.

Receiver 130 receives signals from transmitter(s) 220. The location of capsule 100 within the alimentary canal of subject 300 is determined, at least in part, by the proximity of receiver 130 to transmitter(s) 220. Signal strength indicator or meter 135, integrated on receiver 130, measures the signal strength of transmitter(s) 220. Accordingly, meter 135 provides a proximity based detection means for determining the location of capsule 100 in relation to transmitter(s) 220, disposed at selected medically relevant points on the body of subject 300. Meter 135 identifies the unique signal of each transmitter 220 and measures the signal strength of transmitter(s) 220, thereby determining the proximity of capsule 100 to each specific signaling transmitter 220. Preferably, signal strength information is transmitted by receiver 130 to control circuitry 140 by wire leads. Control circuitry 140 recognizes that receiver 130 is near a transmitter 220 when a pre-programmed signal strength is identified. In this manner, the location of capsule 100 in relation to transmitter(s) 220 disposed on medically relevant points on the body of subject 300 is determined.

Receiver 130 may have one or more antennae for receiving signals or transmissions from transmitter(s) 220. In the preferred embodiment of the present invention, receiver 130 receives radio frequency (RF) communications from transmitter(s) 220. Preferably, receiver 130 requires minimal power because it is always in receiver mode. Signals received by receiver 130 are preferably transmitted to control circuitry 140 via wire leads. Meter 135 may optionally measure the signal strength of transmitter(s) 220 by magnetic induction means.

Control circuitry 140 processes and analyzes the received signals and, accordingly, determines one or more particular actions indicative of the instructions or codes provided by the signals. The actions are determined by correlating the instructions or codes with one or more actions, as described. Control circuitry 140 may optionally be a controller, a processor, a microprocessor or other microcontroller. Control circuitry 140 performs command and control functions as well as data processing. Control circuitry 140 may perform the following functions: maintaining communications connectivity (e.g., controlling network participation), reading and responding to input messages from the transmitter(s), operating the payload mechanisms on command, and transmitting capsule 100 status including present activity and battery charge.

Specifically, control circuitry 140, operatively coupled to receiver 130, receives and processes signals received by receiver 130 from transmitter(s) 220. Control circuitry 140 is programmed to recognize a pre-programmed signal strength for transmitter(s) 220 and at least one pre-programmed location pattern for transmitter(s) 220. Recognition of the pre-programmed signal strength provides confirmation that capsule 100 is disposed near a specific transmitter 220. Recognition of the specified pattern of transmitter(s) 220 created as capsule 100 passes each transmitter 220 provides confirmation of the location of capsule 100 in the gastrointestinal tract of subject 300.

Power source 150 powers control circuitry 140 in order for each of the components to operate. Power source 150 additionally powers any other electrically powered equipment housed by capsule 100. Power source 150 may be a battery, a capacitor or any other known means for providing a power supply.

Power source 150 is operatively connected to storage compartment 120, preferably by wire leads, for powering the actuator mechanism. Storage compartment 120 houses a payload (not shown). The payload is preferably a controlled quantity of a substance to be delivered to a selected site in a human or animal. Non-limiting examples of a suitable substance for use with the present invention include pharmaceutically active compounds, foodstuffs, dyes, radiolabelled markers, vaccines, physiological markers or diagnostic agents. Particularly, the substance may be a medically efficacious material such as, for example, antibiotics, antiviral compounds, chemotherapeutic agents, nutriments (e.g. vitamins, minerals, enzymes), radio isotopes, dyes, tracers, radio opaque materials, growth factors, hormones, steroids, and the like, or any combination thereof. The substance is preferably a medicament for treatment of diseases of the lower gastrointestinal tract. More preferably, the substance is a 5-ASA or a corticosteroid such as budesonide. The medicament can further be an oral contrast agent used to enhance diagnostic images. An example of such a contrast agent is Gastromark® for MRI images and Barium for CT images.

The payload is released from storage compartment 120 when a pre-programmed location pattern of transmitter(s) 220 is recognized by control circuitry 140. Capsule 100 may have an electronically controlled release valve or hatch 125 for dispensing the substance stored in reservoir 120. Capsule 100 may further have an actuator mechanism for operating valve 125, when present. Control circuitry 140 opens and closes valve 125 in accordance with a preset dispensing pattern as described. While not preferred, transmitter(s) 220 may, optionally, send a control signal for instructing capsule 100 to dispense the payload.

Control circuitry 140 controls a release controller 114. Activation of release controller 114 may be triggered by recognition of one or more preset dispensing patterns and/or by instruction from transmitter(s) 220. Power source 150 powers control circuitry 140 in order for each of the electromechanical components to operate during the dispensing period. Release controller 114 is preferably a micro-electromechanical mechanism capable of receiving a signal from release control circuitry 140 and generating a signal having a variable voltage level to the electronically controlled valve 125 for closing valve 125 and controlling the size of the valve opening or degree of opening of valve 125 (in accordance with the voltage level of the received signal). In the simplest case, release control circuitry 140 is a transistor or D/A circuit that provides voltages to the valve 125 causing it to open or close.

Optionally, the voltage level of the signal may determine the size of the valve opening for controlling the quantity of the medicament dispensed at each moment of dispense. In an alternate embodiment, the signal transmitted to the release controller 114 only relays the opening and closing of the valve 125 and not the size of the valve opening.

Dispense or release of the payload is achieved by pressure mechanism 116. Pressure mechanism 116 is located outside storage compartment 120, ensuring that the substance is directed toward valve 125. In the simplest case, pressure mechanism 116 is preferably a spring. Pressure mechanism 116 can also be another type of spring, a piston, or any mechanism for performing the function of pressure mechanism 116. That is, for performing the function of applying pressure to a piston-type member 117 when valve 125 is open to push the piston-type member 117 towards valve 125. As the piston-type member 117 moves towards valve 125 pressure within storage compartment 120 causes the medicament to be dispensed.

Dispense of the payload from storage compartment 120 may also be achieved by osmotic means, by metered pumping mechanism means employing a mechanical or chemical pump, or by any other known means for achieving delivery of a substance.

Transmitter(s) 220 are preferably simple beacon transmitters for sending a signal to receiver 130. Each transmitter 220 has a unique identification means for differentiating it from other transmitter(s) 220. The identification means may optionally be a specific data pattern, a key, or a coded transmission frequency. Transmitter(s) 220 may send a signal by any means known in the art. For example, transmitter(s) 220 may propagate radio frequency signals, electromagnetic inductive signals or may employ other forms of telecommunication. Transmitter(s) 220 may be active radio frequency identification (RFID) tags.

Control circuitry 140 may be programmed to require a preset pattern of information prior to dispensing the payload of capsule 100. The location(s) of transmitter(s) 220 on the body of subject 300 correspond with medically relevant locations in the gastrointestinal tract. Moreover, placement of transmitter(s) 220 on the body of subject 300 will vary depending on where in the gastrointestinal tract release of the payload is desired. Transmitter(s) 220, placed on subject 300, form a pattern of beacon signal locations that is received by receiver 130, measured by meter 135 and recognized by control circuitry 140. The pattern of information, recognized by control circuitry 140 operates as a safety, ensuring that capsule 100 has passed through identified gateways prior to instructing payload release. A pattern of instruction may be simple; for example, when receiver 130 recognizes a transmitter A, it transmits that information to control circuitry 140, programmed to dispense the payload upon recognition of transmitter A. Control circuitry 140 then operates the mechanism for dispensing the payload. The pattern of instruction may optionally be more complex; for example when receiver 130 recognizes a transmitter A, followed by a transmitter B, followed by a transmitter C, it transmits that information to control circuitry 140, programmed to dispense the payload upon recognition of transmitter A, followed by transmitter B, followed by transmitter C. Control circuitry 140 then operates the mechanism for dispensing the payload. The preset pattern of instructions provides verification that a specific targeted area of the gastrointestinal tract has been reached prior to dispensing the payload.

Electronically controlled valve 125 is preferably a microelectromechanical mechanism capable of being electrically controlled by a signal having a variable voltage levels. Each voltage level corresponds to a different size opening for the valve opening and one voltage level (or no voltage at all, i.e., no signal) corresponds to valve 125 being closed. Valve 125 is characterized as a microfluidic valve for controlling the movement of minute amount of liquids or gases in a miniaturized system.

Figure 4:
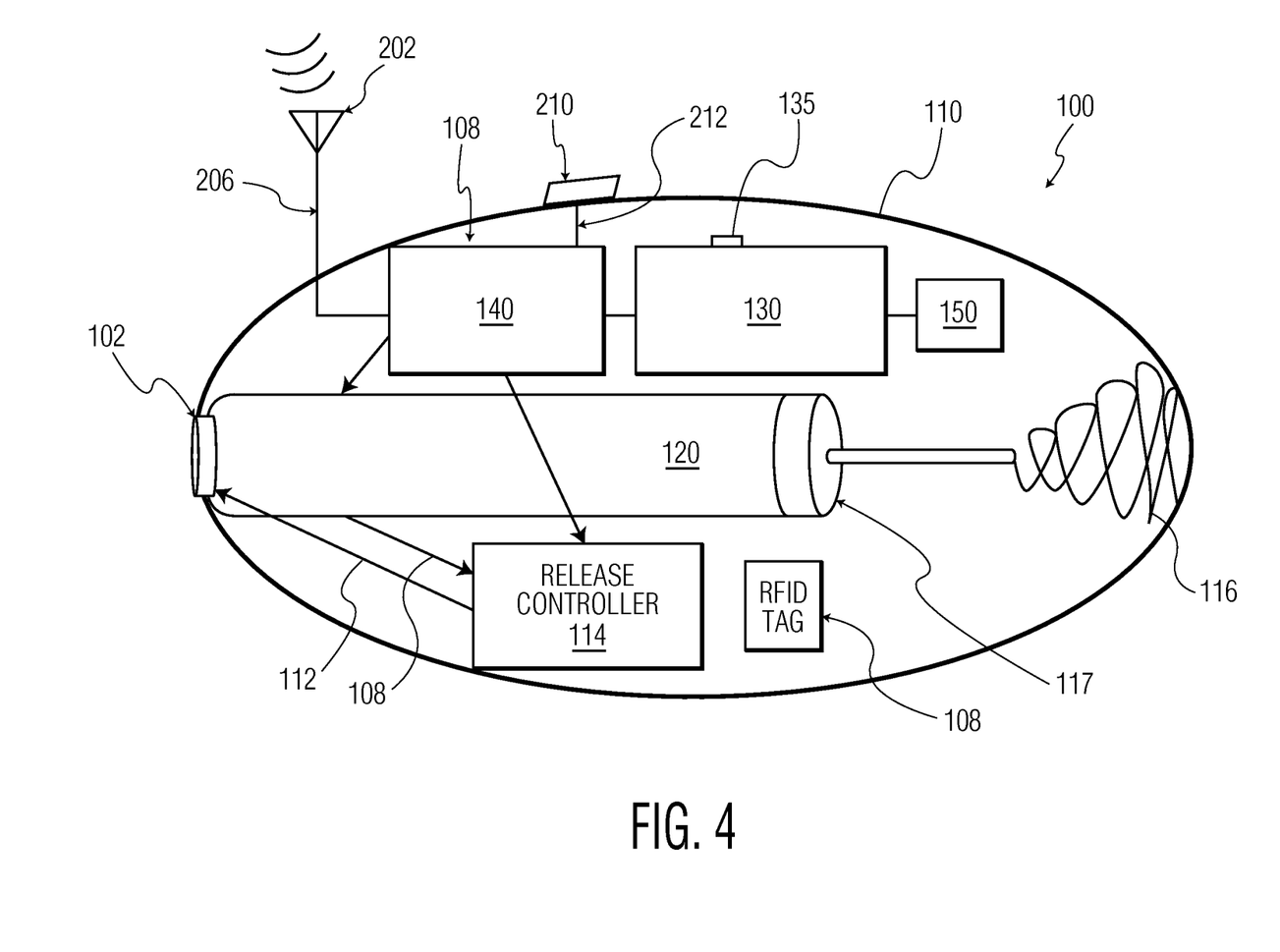
FIG. 4 is a schematic diagram of an electronic pill in accordance with a second embodiment of the present invention.

In an alternate embodiment of the present invention illustrated in FIG. 4, storage compartment 120 is a micro-syringe, whereby pressure applied to a plunger of the syringe dispenses the medicament via a needle tip of the micro-syringe. In this embodiment, opening 102 replaces valve 125. It is contemplated, however, that a check valve is disposed at the needle tip of the micro-syringe to avoid leakage of the medicament during time periods within the dispensing time period where there should be no dispensing according to the preset dispensing timing pattern, and/or for controlling the quantity of medicament dispensed during the dispensing time period.

Pressure mechanism 116 is located outside storage compartment 120, ensuring that the medicament is directed toward opening 102. In the simplest case, the pressure mechanism 116 is preferably a spring. Pressure mechanism 116 can also be another type of spring, a piston, or any mechanism for performing the function of pressure mechanism 116.

In another alternate embodiment, storage compartment 120 is kept under pressure to assure that a proper quantity of medicament is dispensed in accordance with the degree of openness of valve 125, without the need for pressure mechanism 116. The pressure can be monitored by a pressure sensor which relays the monitored pressure to control circuitry 140. If the pressure is outside a predetermined range, the circuitry 140 can then adjust the valve opening to increase or decrease the pressure. Naturally, the pressure of storage compartment 120 can be different for each medicament and can depend on the medicament's viscosity.

The signal transmitted by transmitter(s) 220 may be compromised due to the size and/or weight of subject 300. A signal may not transmit readily through an individual having substantial body mass. Thus, control circuitry 140 may be calibrated to recognize an altered signal measurement from meter 135 for confirming the proximity of receiver 130 to transmitter(s) 220 for a particular individual, taking into account the effectiveness of transmitter(s) 220 in relation to the individual's weight and size. Therefore, two individuals can be administered the same medicament utilizing two different calibrations. Moreover, signal strength can be determined using a look-up table which correlates one or more characteristics of a person with one or more preset dispensing patterns. For example, a look-up table can correlate at least one of age, gender, weight, etc. with preset signal strength measurements which correspond with preset signal strength measurements. Subject 300 would then be administered a capsule 100 which is programmed with one of the determined preset signal strength measurements. Accordingly, capsule 100 of the present invention enables the same medicament to be administered to different individuals using different signal strength measurements.

Moreover, a look-up table or other data structure can be assessed by circuitry 140 which correlates pressure, degree of valve opening, and other parameters, such as period of time in the dispensing time period, for determining, for example, the degree of valve opening by knowing the pressure, and vice versa. Based on the information obtained by assessing the look-up table, circuitry 140 can then adjust the pressure, the valve opening, etc. These adjustments can be made in order to substantially track the preset dispensing pattern programmed within capsule 100.

Referring again to FIGS. 2 and 3, capsule 100 is ingested by, for example, human subject 300, and enters the alimentary system 310 of subject 300. Transmitter(s) 220 are attached to the body of subject 300 in various predetermined locations. Predetermined locations identify known junctures in the gastrointestinal tract such as, for example, the ascending colon, the transverse colon, the descending colon, the ileum, the rectum, etc.

In a preferred embodiment of the present invention, a wearable apparatus 250 is worn around the waist of the subject 300, as illustrated. Wearable apparatus 250 houses at least one transmitter 220. Wearable apparatus 250, when worn by subject 300, is configured to place transmitter(s) 220 at specific locations on the body. The location of transmitter(s) 220 in wearable apparatus 250 correspond to medically relevant target areas of the gastrointestinal tract of the subject 300. Wearable apparatus 250, while shown as a belt, may optionally be a shirt, a suit or any other means for effectively securing transmitter(s) 220 to subject 300. Optionally, transmitter(s) 220 may be pinned to subject 300 or worn in pockets of a jacket or shirt worn by subject 300. Transmitter(s) 220 may alternately be housed in plasters 251 that are affixable to the subject 300 at the predetermined locations. It is contemplated that any combination of the above may be employed.

Wearable apparatus may optionally house one or more receiver(s) or transceiver(s) for receiving information from capsule 100 such as by way of non-limiting example, diagnostic or location information.

Transmitter(s) 220 transmit a wireless signal to capsule 100 upon determination that a selected site in the alimentary canal of the human 310 has been reached by capsule 100. The signal sent by transmitter(s) is an instruction to dispense the substance from storage compartment 120.

FIG. 3 illustrates medically relevant locations on the body of the subject where transmitter(s) 220 are placed for treatment of an illness of the gastrointestinal tract. Location A marks the cecum, located between the small and large intestines. Location B marks the hepatic flexure and the beginning of the transverse colon. Location C marks the spenic flexure and the beginning of the descending colon. Wearable apparatus 250, when employed as a belt or garment, appropriately situates transmitter(s) 220 so that when wearable apparatus 250 is worn by subject 300, transmitter(s) 220 are appropriately placed at Location B and/or Location C. Wearable apparatus 250 thereby provides a simple, efficient and easily replicated means for sending signals to capsule 100. Moreover, wearable apparatus provides means for various coded commands and/or information to be readily transmitted to capsule 100.

The specific area targeted for treatment is determined based on patient history of subject 300 such as history of disease or clinical examination. A non-limiting example of such information is the result of a recent endoscopic examination. To ensure that capsule 100 does not dispense the medication before the targeted treatment location is reached, control circuitry 140 of capsule 100 is programmed to receive a specific pattern of transmissions from transmitter(s) 220, or release profile, before releasing the medication. The release profile may include a delivery pattern, a targeted location and a rate of delivery. By way of non-limiting example, for the treatment of a subject 300 suffering from ulcerative colitis, the selected target location may be the area from the descending colon to the rectum. In this case, passage of capsule 100 near transmitter C is tracked by proximity of receiver 130 to transmitter(s) C as determined by meter 135. Receiver 130 relays proximity information to control circuitry 140, which recognizes passage of capsule 100 near transmitter C as a prerequisite to dispense. Receiver 130 may optionally receive a control signal from transmitter(s) 220 to dispense the payload. Capsule 100 dispenses a medication according to the setting programmed into capsule 100, or according to a communicated command from transmitter 220. In another example, the targeted area for delivery of medication is the area of the descending colon. Capsule 100 is thus programmed to receive a transmission from location A, followed by a transmission from location B, followed by a transmission from location C, in order to finally release the medication at location C. This procedure reduces the chance that a lone transmission from location C could accidentally cause capsule 100 to prematurely release the medication in the stomach, which is relatively nearby the splenic flexure of the descending colon.

Figure 5:
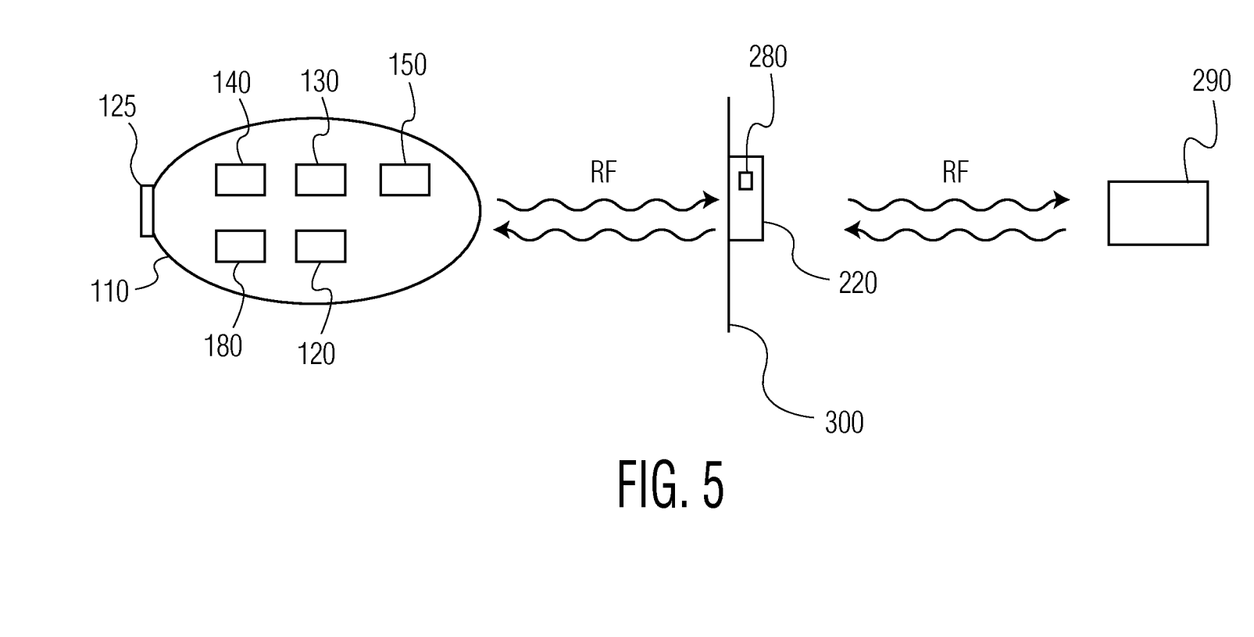
FIG. 5 is a schematic diagram illustration of a system employing the electronic pill of FIG. 4.

In an alternate embodiment of the present invention illustrated in FIGS. 4 and 5, capsule 100 further has at least one transmitter(s) and/or transceiver(s) 180 for transmitting a signal from capsule 100. Capsule transmitter(s) or transceiver(s) 180 may transmit information relating to location of capsule 100, the environment surrounding capsule 100, or information relating to the status of capsule 100. Other clinically relevant information may be also transmitted by capsule 100.

As illustrated in FIG. 5, capsule 100, ingested by subject 300, communicates via radio frequency signals with external transceiver(s) 280 of transmitter(s) 220, which are attached to body of subject 300. Optionally, transceiver(s) 280 may also possess means for communicating via radio frequency electromagnetic signals with a remote medical monitoring station 290. In addition to delivering a command signal to capsule 100, transceiver(s) 180 can be programmed to collect data and recognize medical conditions which require attention and/or treatment (e.g., change in heart rate, breathing, body temperature etc.) and issue commands to capsule 100 to take remedial action (e.g., deployment of medically efficacious drugs) while sending signals to the remote medical monitoring station 290 to alert medical personnel as to the medical condition of subject 300. It is envisioned that capsule 100 may further have means for acquiring samples from the gastrointestinal tract of subject 300.

Capsule 100 may additionally optionally include a miniaturized visualizing apparatus such as an optical camera and optionally a light source (e.g., from a LED or flash unit). When present, visual information is transmitted to transmitter(s) 220 via transmitter(s) or transceiver(s) 180.

Referring again to FIG. 4, capsule 100 may optionally include an RFID tag 108 for tracking, identification, inventory and other purposes using an RFID reading system. RFID tag 108 can also be used to determine if capsule 100 was administered by a caregiver or taken by the person, and if so, RFID tag 108 can be used to determine the general location of capsule 100 within the gastrointestinal tract.

Capsule 100 may further include a piezo-electric element and associated circuitry 210 for remotely controlling capsule 100. Element 210 is preferably affixed to housing 110 and is capable of being vibrated at one or more predetermined frequencies. The vibration is caused by placing an ultrasound probe, hydrophone or other vibration-causing device in proximity to the person.

The frequencies caused by element 210 are converted to electrical signals by the associated circuitry. The electrical signals are transmitted to timing circuitry 110 via wire lead 212 where they are processed for determining an action to perform. The action can be one of the actions described above with reference to the signals provided to the timing circuitry 110 via wire leads 206. The action is preferably determined by correlating the vibration of element 210 to an action using a data structure, such as a look-up table, stored within control circuitry 140

In this embodiment, capsule 100 is able to communicate with transmitter/receiver 280 via antenna 202 (or piezo electric equivalent) of a dosage management system. The transmitter/receiver forwards commands determined by remote medical monitoring station 290. Remote medical monitoring station 290 is a computing device, such as a personal computer, which may be connected to the Internet or other network, such as a LAN. Remote medical monitoring station 290 receives patient vital sign information electronically from advanced monitoring systems including pulse, oxygen level from a pulse-oximeter, EKG, blood pressure, temperature, or from a manual computer entry, such as from a keyboard. The patient or doctor may enter information into remote medical monitoring station 290, such as the degree of pain which typically cannot be measured directly.

Capsule 100 may further have means for performing diagnostic functions such as testing the surrounding matter or fluid for pH (alkalinity or acidity), or the presence or concentration of various salts, minerals or other selected materials.

Due to variability of patient-to-patient body type it may be difficult to predict the signal level received by capsule 100. Another embodiment of the present invention employs a test capsule 100. Test capsule 100 has a transmitter housed therein. Test capsule 100 sends the signal transmitted by transmitter(s) 220 to a calibration system to determine signal strength. In this manner, it may be ensured that transmitter(s) 220 have sufficient power to reach capsule 100 internally.

Accuracy in determining the location of capsule 100 may optionally be aided by additional sensing means. Capsule 100, for example, may contain a simple sensor for pH. pH rises as it passes through the intestines. A pH greater than about 6.0-7.0 combined to proximity to transmitter(s) 220 would reliably indicate that capsule is located in the colon at the position of transmitter(s) 220. Alternatively, capsule 100 may include a sensor for colonic bacteria or enzymes. For example, a sensor for azoreductase would indicate that capsule 100 is located somewhere in the colon of subject 300. Proximity to transmitter(s) 220 would then reliably indicate where in the colon capsule 100 is located.

Capsule 100 may optionally have timing means for aiding in determination of its location and proper timing of dispense of the substance in the gastrointestinal tract. For example, a start timer mechanism 112 may be employed. When capsule 100 is taken or administered, the sensor senses the capsule 100 is administered to a person or animal. In another embodiment, this can be achieved by dissolving a thin, water soluble coating that separates two electrical contacts, enabling the switch to close the circuit. In still another embodiment, the switch is manually triggered by the subject.

Capsule 100 can further be used for diagnostic purposes. A common problem in multi-modal imaging (e.g. any combination of CT, PET, MRI, Ultrasound, X-Ray, etc.) is the registration of images. Between images, patient motion causes difficulties in 'registering' different images to one another. Patient motion includes walking between the exams as well as voluntary and involuntary internal motions such as breathing, heart beating, and digestion. Capsule 100 can be used to release contrast agents in particular areas that can be estimated by time in order to minimize the contrast agent required or concentrate it in a particular area. Use of contrast agent does not only register the images in terms of location, but in terms of time. This fourth dimension can improve the accuracy of co-registration.

While not preferred, it is envisioned that wearable apparatus 250 may further have one or more sensors for aiding in determining the location of capsule 100 without physical contact by emitting an electromagnetic field or beam and monitoring changes in the field. Sensors, when employed, measure the current flow between the sensors and capsule 100. Capsule 100, when sensed, changes the dielectric constant between a pair of sensor plates.

Sensors, when employed, may be inductive or capacitive sensors. Sensors are high frequency oscillators that create a field in the close surroundings of the sensing surface. The presence of a capsule 100 in the operating area causes a change of the oscillation amplitude of sensors. The rise or fall of such oscillation is identified by a threshold circuit that changes the output state of the sensors. Inductive sensors are employed for a metallic embodiment of capsule 100. Capacitive sensors are employed for a non-metallic embodiment of capsule 100.

Photoelectric sensors may also be employed. Photoelectric sensors use light sensitive elements to detect capsule 100 and are comprised of an emitter (light source) and a receiver. The sensors may also be magnetic sensors. Magnetic sensors are actuated by the presence of a permanent magnet housed in capsule 100.

The present invention has been described with particular reference to the preferred embodiments. It should be understood that the foregoing descriptions and examples are only illustrative of the present invention. Various alternatives and modifications thereof can be devised by those skilled in the art without departing from the spirit and scope of the present invention. Accordingly, the present invention is intended to embrace all such alternatives, modifications, and variations that fall within the scope of the appended claims.

The invention claimed is:

1. A system for delivering a substance to a selected site in an alimentary canal of a body of a human or animal, the system comprising:
   at least one transmitter disposed in a housing in proximity to a medically relevant site on the body and transmitting signals; and
   an ingestible capsule for receiving the signals, collecting data, and releasing the substance, the capsule comprising:
      a compartment for storing the substance;
      a releasing device for releasing the substance from the compartment;
      a receiver suitable for receiving the signals through a tissue of the body;
      a processor for storing a programmed set of instructions for recognizing patterns of the signals, each of the patterns is designed to identify a site in the body, and for initiating the releasing of the substance upon recognizing of a specific pattern; and
      an electronic power source;
   wherein the receiver comprises a proximity based detector for measuring proximity of the receiver to the at least one transmitter.

2. The system of claim 1, wherein the selected site for delivering the substance is a lower gastrointestinal tract of the body.

3. The system of claim 1, wherein the selected site for delivering the substance is a colon of the body.

4. The system of claim 1, wherein the housing comprises a wearable apparatus.

5. The system of claim 1, wherein the housing comprises a plaster that is attachable to the body.

6. The system of claim 1, wherein the proximity based detector comprises a signal strength meter.

7. The system of claim 1, wherein the capsule further comprises a dosage pump.

8. The system of claim 1, wherein the capsule further comprises a transceiver that is programmed to transmit the data collected by the capsule.

9. The system of claim 8, wherein the housing further comprises a transceiver that is programmed to issue commands to the capsule for taking a specified action based upon the collected data.

10. The system of claim 1, wherein the capsule further comprises a pH sensor for locating the capsule.

11. The system of claim 1, wherein the capsule further comprises a sensor for colonic bacteria or enzymes for locating the capsule.

12. The system of claim 1, wherein the capsule further comprises diagnostic, analytical, treatment or imaging devices.

13. A system for delivering a substance to a selected site in an alimentary canal of a body of a human or animal, the system comprising:

a wearable apparatus attachable to the body and having at least one transmitter for sending wireless signals and a receiver for receiving information; and an ingestible capsule for collecting the information and releasing the substance, the capsule comprising:

a storage compartment for storing the substance;

a releasing device for releasing the substance from the storage compartment upon recognizing of a specific pattern;

a receiver for receiving the wireless signals through a tissue of the body, the signals forming recognizable patterns, each of the patterns is designed to identify a site in the body where the substance is to be released;

a transmitter suitable for transmitting the information through the tissue of the body; and an electronic power source.

14. The system of claim 13, wherein the capsule further comprises a transceiver for sending the information from the capsule and the wearable apparatus further comprises a transceiver that is programmed to issue commands to the capsule for taking remedial action based upon the collected information.

15. The system of claim 13, wherein the capsule further comprises a pH sensor for locating the capsule and/or a sensor for colonic bacteria or enzymes for locating the capsule.

* * * * *